US008515008B2

(12) United States Patent
Ullberg et al.

(10) Patent No.: US 8,515,008 B2
(45) Date of Patent: Aug. 20, 2013

(54) APPARATUS AND METHOD FOR X-RAY FLUORESCENCE ANALYSIS OF A MINERAL SAMPLE

(75) Inventors: Anders Ullberg, Åby (SE); Erik Odén, Täby (SE); Ragnar Kullenberg, Oskarström (SE); Frédrik Danielsson, Solna (SE)

(73) Assignee: Orexplore AB, Kista (SE)

( * ) Notice: Subject to any disclaimer, the term of this patent is extended or adjusted under 35 U.S.C. 154(b) by 384 days.

(21) Appl. No.: 12/735,425

(22) PCT Filed: Feb. 2, 2009

(86) PCT No.: PCT/EP2009/000656
§ 371 (c)(1),
(2), (4) Date: Nov. 1, 2010

(87) PCT Pub. No.: WO2009/098009
PCT Pub. Date: Aug. 13, 2009

(65) Prior Publication Data
US 2011/0044426 A1    Feb. 24, 2011

(30) Foreign Application Priority Data
Feb. 4, 2008   (EP) .................................... 08151006

(51) Int. Cl.
*G01N 23/223* (2006.01)
*G01N 23/083* (2006.01)
*G01N 23/10* (2006.01)
*G01F 23/00* (2006.01)

(52) U.S. Cl.
USPC .................... 378/45; 250/360.1; 250/491.1

(58) Field of Classification Search
USPC ............ 378/44–46, 48, 49, 145, 146, 204, 378/210; 250/253–255, 304, 306–308, 358.1, 250/360.1, 362, 363.01, 370.01, 370.08, 250/370.09, 371, 393, 395, 428, 432, 433, 250/440.11, 491.1, 492.1, 492.3
See application file for complete search history.

(56) References Cited

U.S. PATENT DOCUMENTS 3,394,263 A    7/1968  Baker
3,927,318 A   12/1975  Macovski
(Continued)

FOREIGN PATENT DOCUMENTS

| EP | 1811291 A1 | 7/2007 |
| GB | 1040321 A | 8/1966 |
| JP | 1006850 | 1/1989 |
| SU | 1570658 | 6/1990 |
| SU | 1672325 | 8/1991 |

OTHER PUBLICATIONS

International Search Report.
Erkhardt, Kh. "X-ray Fluorescent Analysis," Moscow, 1985, pp. 205-206.
Russian Office Action dated Oct. 2, 2012 issued in corresponding Russian Application 2010136936.

*Primary Examiner* — Anastasia Midkiff
(74) *Attorney, Agent, or Firm* — Harness, Dickey & Pierce, P.L.C.

(57) ABSTRACT

An apparatus and a method for X-ray fluorescence analysis of a mineral sample is disclosed. The apparatus comprises an X-ray source (2) for generating an X-ray beam to irradiate the mineral sample; at least one fluorescence detector (4,5) for measuring fluorescent radiation emitted by the mineral sample when irradiated by the X-ray beam; and a processing unit for providing an analysis of the mineral sample based on the measurements made by the at least one fluorescence detector (4,5). Further, the apparatus comprises a sample container (3) arranged to hold the mineral sample during the irradiation, wherein the sample container is arranged to provide at least two different irradiation paths through said mineral sample during irradiation. An advantage with this arrangement is that it enables analysis of elements having a wide range of atomic numbers in a single sample with improved reliability and accuracy. This results in maximized detectability for a wide range of elements, while reducing the number of samples that needs to be prepared. The present invention also leads to simplified sample preparation, and to a faster and more cost-efficient analysis. This makes the apparatus particularly useful for field use.

29 Claims, 3 Drawing Sheets

(56) References Cited

U.S. PATENT DOCUMENTS 6,668,039 B2 * 12/2003 Shepard et al. .................. 378/47
7,120,226 B2 * 10/2006 Ledoux et al. .................. 378/57
7,215,733 B2    5/2007 Nabatame
2006/0098773 A1 *  5/2006 Peschmann ..................... 378/57
2007/0211852 A1    9/2007 Matoba
2007/0269004 A1 * 11/2007 Matoba et al. .................. 378/45
2007/0274441 A1 * 11/2007 Fukai et al. ..................... 378/45

* cited by examiner

APPARATUS AND METHOD FOR X-RAY FLUORESCENCE ANALYSIS OF A MINERAL SAMPLE

TECHNICAL FIELD

The present invention relates to an apparatus and method for X-ray fluorescence analysis of a mineral sample.

BACKGROUND OF THE INVENTION

X-ray fluorescence (XRF) analysis is widely used for chemical analysis of materials, and one of the applications is within geochemistry, e.g. for prospecting and mining. During analysis in such applications, mineral samples are irradiated by an X-ray beam, whereby fluorescent radiation is emitted by elements contained therein. The fluorescent radiation can be analyzed, for instance, by energy dispersive analysis, whereby the energies of the photons are analyzed, and the intensity of each characteristic radiation frequency may be directly related to the amount of each element in the mineral sample. Thus, the elements present in the mineral sample, as well as the quantities of said elements, can be determined.

Traditionally in geochemistry applications, all material that were to be analyzed, such as drill cores collected during prospecting, had to be sent to a laboratory for analysis. Today however, there are instruments available to perform X-ray fluorescence analysis in situ, thereby providing a quicker response. Examples of such portable, and often handheld, instruments are commercially available from, for example, Niton.

For performing analysis in situ, there are typically two alternatives available for sample preparation. According to the first alternative, the instrument is simply directed towards the ground or against a plastic bag holding the sample, i.e. the analysis is performed without any real sample preparation. According to the second alternative, a sub-sample is picked out and packed in a cup, which is inserted in the instrument and the analysis is performed on the sample in the cup. To improve reliability of the analysis, the sample preparation here typically involves drying the sample at room temperature or in a drying chamber, grinding the sample to achieve a fine-grained structure, and then carefully packing the fine-grained sample into the cup to ensure a uniform density. However, these known methods often only provides a measure related to the surface layer of the sample, and the samples are normally required to be relatively thin, thereby providing a measure on only a very limited amount of material.

Unfortunately, the level of uncertainty associated with the in situ analysis is often considerable, and, even as the sample has been thoroughly prepared, the in situ analysis often needs to be complemented with a confirmatory laboratory analysis. This will normally reduce efficiency and slow down the field work. Further, known in situ methods are often tedious and cumbersome to use. Thus, there is a need for in situ X-ray fluorescence analysis that provides more reliable analysis and reduces the required sample preparation. There is also a need for more cost-efficient ways of providing reliable chemical material analyses on the field.

SUMMARY OF THE INVENTION

In view of the above, an object of the invention is to solve or at least reduce the problems discussed above. In particular, an object is to achieve improved reliability for in situ analysis, while reducing the required sample preparation needed.

According to an aspect of the invention, there is provided an apparatus (1) for X-ray fluorescence analysis of a mineral sample comprising:

an X-ray source (2) for generating an X-ray beam to irradiate the mineral sample;

at least one fluorescence detector (4,5) for measuring fluorescent radiation emitted by the mineral sample when irradiated by the X-ray beam;

a processing unit for providing an analysis of the mineral sample based on the measurements made by the at least one fluorescence detector (4,5), wherein said apparatus (1) further comprises:

a sample container (3) arranged to hold the mineral sample during the irradiation, wherein the sample container is arranged to provide at least two different irradiation paths through said mineral sample during irradiation.

An advantage with the arrangement is that it enables analysis of elements having a wide range of atomic numbers in a single sample with improved reliability and accuracy. This results in maximized detectability for a wide range of elements, while reducing the number of samples that needs to be prepared. The present invention also leads to simplified sample preparation, and to a faster and more cost-efficient analysis.

As the accuracy and reliability of analysis performed in situ is improved, the need for confirmatory laboratory analysis is reduced. This means that informed decision can be made promptly and continuously as prospecting proceeds, without waiting for laboratory results, and thus the prospecting process can be accelerated and made more efficient. Furthermore, a reduced need for laboratory analysis leads to enhanced cost efficiency, not only as the in situ analysis typically is less expensive per sample than laboratory analysis, but also as additional sample handling and transportation associated with laboratory analysis is avoided.

The present invention is based on the understanding that, in order to be detected, the fluorescent radiation needs to have sufficiently high energy to escape the mineral sample without excessive attenuation. The fluorescent radiation and absorption of elements having low atomic numbers differs significantly from elements having high atomic numbers. By utilizing a sample having two or more irradiation paths through the sample, and preferably irradiation paths of various lengths through the material, each element of interest can be analyzed using the irradiation path most appropriate. Hereby, even fluorescent radiation of low energy can penetrate out from the sample and be detected by the fluorescence detector. By means of the present invention, an effective compromise between sensitivity and accuracy/resolution can be achieved for essentially all materials. For elements having low atomic numbers a relatively short path length may be used (with low energy K-radiation), and for elements having high atomic numbers (with high energy K-radiation) longer paths may be used. In this latter case, the ability to accurately detect the elements is increased, since the path may cross more atoms of the element. By an additional variation of the excitation energy, an optimal choice of energy can be made, in particular close to the K edge energy, for analysis of various elements.

The apparatus further preferably comprises controller means to adjust an X-ray tube voltage of said X-ray source in accordance with the length of the irradiation paths. This means that the energy of the X-ray beam is adapted to the excitation energy of the elements which are most appropriate to analyze for the current irradiation path, with improved reliability and accuracy as a result.

The sample container may be rotatably arranged, enabling the irradiation path through the mineral sample to be varied, which may enhance the reliability and the accuracy of the analysis. Hereby, the requirement on e.g. uniformity and packing of the sample becomes lower, since a multitude of irradiation paths in different directions can easily be obtained. Rotation of the sample may occur between measurements of different samples, or between consecutive measurements on the same sample. However, preferably the sample is being rotatable during said irradiation.

Furthermore, the sample container may have a uniform cross-section, such as a circular cross-section, wherein the rotational symmetry allows the mineral sample to be analyzed utilizing multiple irradiation paths having essentially the same length, whereas the geometry between X-ray source, the fluorescence detectors and the sample container may be kept constant. This may also reduce variations in the results of the analysis due to the sample compositions. However, alternatively the sample container may have a non-uniform cross-section, such as, for example, an elliptical cross-section. Hereby, rotation of the sample container allows the irradiation path through the sample, and the length thereof, to be varied in a very simple way.

According to one embodiment, the sample container may have an essentially tapered form. The tapering form of the sample container may e.g. be in the form of a cone or a frustro-conical cone. Thus, the length of the irradiation path may be varied by moving the X-ray beam, which may typically be perpendicular to the tapering direction, in the tapering direction.

According to a preferred embodiment of the present invention, the sample container is arranged to provide at least five different irradiation paths through the mineral sample during irradiation, said irradiation paths preferably being of different lengths through said mineral sample. Even more preferably the apparatus may be arranged to scan the irradiation beam through a part of the sample container, thereby provide a multitude of varying irradiation paths through said mineral sample during irradiation. In this way a variety of elements can be analyzed with an improved reliability and accuracy using a single sample.

The length of the irradiation path through the mineral sample is preferably in the range between 30 mm and 80 mm, and most preferably relatively evenly distributed in said range so that it varies between essentially said end values. The chosen range depends inter alia on the atomic numbers of the elements currently analyzed. The shorter irradiation paths of the interval typically are used to study elements having atomic number 40 to 50, whereas the longer irradiation paths of the interval typically are used to study elements having atomic numbers 51 to 80. However, these lengths are merely indicative and may vary, e.g. due to the sample conditions. As understood by a person skilled in the art these intervals can further be split up into sub-ranges for increased accuracy. Also, irradiation paths having other lengths may be utilized to study other atomic numbers.

Further, the X-ray tube voltage can be adapted to the excitation energy of the elements analyzed. The X-ray tube voltage may typically be varied between 40 kVp and 160 kVp, where the lower voltages of the interval typically are used for atomic numbers 40 to 50 and the higher voltages of the interval typically are used for atomic numbers 51 to 80. It should be noted that, these values are merely indicative and may vary due to the measurement conditions. As understood by a person skilled in the art these intervals can be further split up into sub-intervals for increased accuracy. Also, voltages outside these intervals may be used.

According to an embodiment of the present invention, there may be provided a transmission detector for measuring X-ray transmission through the mineral sample during irradiation. Further, correction means to correct the measured fluorescent radiation due to variations in composition of the mineral sample based on the measurements made by the transmission detector. Thus, the analysis of the mineral sample may be compensated for variations in the attenuation of the fluorescent radiation, which may arise, for example, due to variations in composition of the mineral sample, such as density. This results in improved reliability and accuracy of the X-ray fluorescence analysis and makes advanced sample preparation obsolete.

The apparatus also preferably comprises an energy spectrum analyzer for separately measuring the $K_\alpha$ and $K_\beta$ components of the fluorescent radiation. Thus, the $K_\alpha$ and $K_\beta$ components of the fluorescent radiation can be separately compensated for variations in attenuation. As the attenuation typically differs between $K_\alpha$ and $K_\beta$ components this improves the reliability and accuracy of the X-ray fluorescence analysis.

Such compensation is per se known from U.S. Pat. No. 3,927,318, said document hereby incorporated by reference. This document disclose a fluorescent imaging system for selectively imaging trace amount of specific materials. The arrangement includes a compensation system that can be used to minimize the effect of the absorption of the fluorescent radiation by introducing a gain function. A more exact compensation for fluorescent attenuation can be achieved through the separation of the various components of the fluorescent radiation into $K_\alpha$ and $K_\beta$ components. It also has an X-ray beam attenuation compensator. A more accurate correction for the X-ray beam attenuation can be obtained by using the actual attenuation or density values in the cross section. However, U.S. Pat. No. 3,927,318 is related to a totally different field, and also differs from the present invention inter alia in that it does not involve a sample container.

The at least one X-ray fluorescence detector and the transmission detector may preferably be located apart from each other. This minimize the overlap in the measured signals, and thereby improves the reliability and accuracy of the apparatus. The transmission detector is preferably arranged directly opposite to the X-ray source, whereas the fluorescence detector(s) is/are hereby arranged in a direction up to, and preferably close to, 90 degrees angled to this primary radiation path. This also reduces the Compton radiation. The differential cross-section for Compton radiation has a radiation minimum at 90 degrees. Consequently, such an arrangement reduces the background radiation below the fluorescence peaks.

In a preferred embodiment of the invention, a first and a second X-ray fluorescence detector may be arranged on opposite sides of the sample container, and preferably at essentially right angles to the principal direction of the X-ray beam. Through this arrangement, the aggregated pulse response from the first and second fluorescence detector is independent of where in the sample the fluorescent radiation emanates. The arrangement of the fluorescence detectors perpendicular to the principal direction of the X-ray beam minimizes the effect of Compton scattering.

The apparatus is preferably portable, and easy to bring along for field use. This typically means that the apparatus can be lifted by one or two persons, and that it is small enough to be transported in an ordinary vehicle, such as in a station wagon, a van, a pick-up truck, or an SUV. Further, the apparatus may preferably be arranged with an outer housing or casing, enabling a robust instrument which may endure the harsh environment that may occur during field work. This may include considerable temperature differences during use, outdoors or indoors, e.g. in an air condition van, or during or transportation in a van, or on the back of a pick-up truck. The instrument should also endure shocks that may arise under in these circumstances. Furthermore, the casing/housing material preferably comprises lead to prevent any radioactive radiation to escape and affect the environment or any persons nearby.

According to another aspect of the invention, there is provided a method for X-ray fluorescence analysis of a mineral sample comprising the steps:

providing a mineral sample in a sample container;
irradiating said mineral sample with an X-ray beam;
measuring fluorescent radiation emitted by the mineral sample when irradiated by the X-ray beam; and
providing an analysis of the mineral sample based on the measurements of the fluorescent radiation;
wherein the sample container is arranged to provide at least two different irradiation paths through said mineral sample during irradiation.

Hereby, similar advantages as discussed above in relation to the first aspect of the invention are obtainable.

Other objectives, features and advantages will appear from and be further elucidated by the following detailed disclosure, from the attached dependent claims as well as from the drawings.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, where the same reference numerals will be used for similar elements, wherein.

DETAILED DESCRIPTION OF PREFERRED EMBODIMENTS

Figure 1:
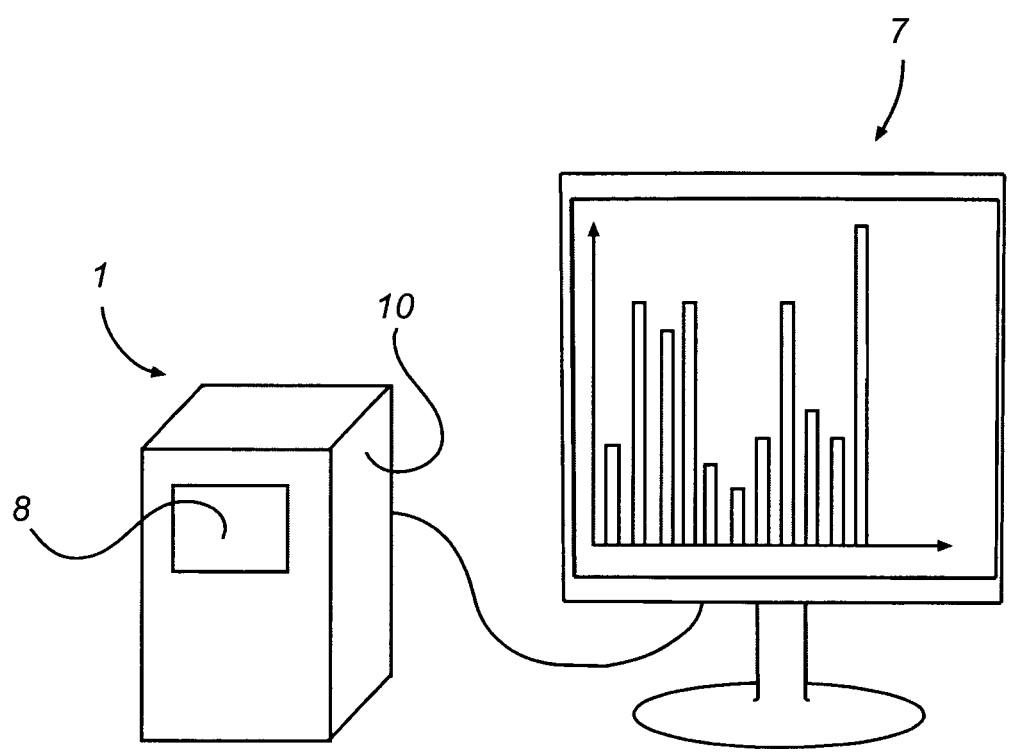
FIG. 1 illustrates a schematic view of an apparatus for X-ray fluorescence analysis of a mineral sample in accordance with an embodiment of the present invention.
Figure 2:
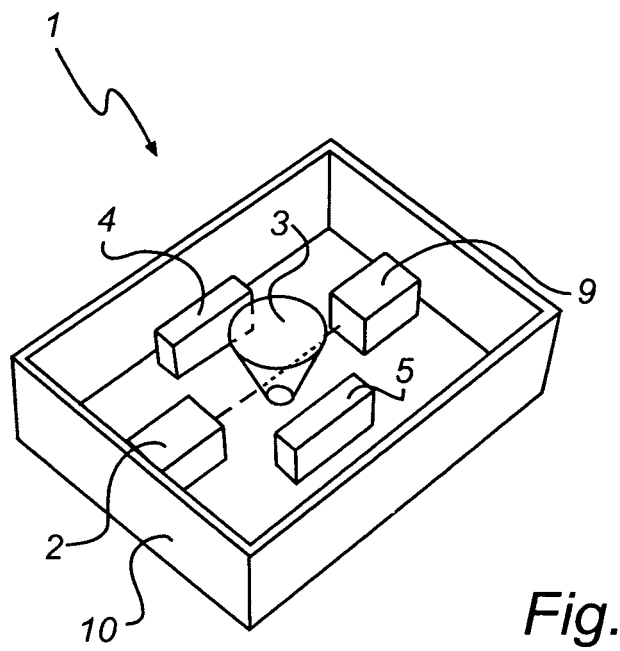
FIG. 2 illustrates a schematic view of a measurement set-up inside the apparatus for X-ray fluorescence analysis of FIG. 1.
Figure 3:
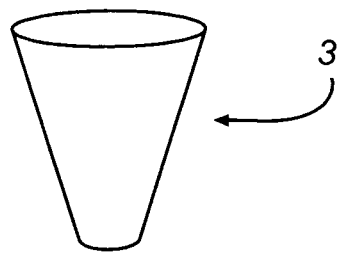
FIG. 3 illustrates a schematic view of a sample container to be used in the apparatus of FIG. 1.
Figure 4A:
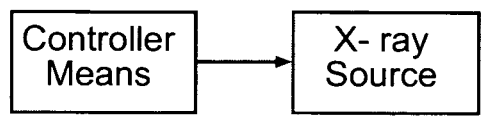
FIGS. 4a and 4b illustrates a block diagram of the apparatus for X-ray fluorescence analysis of a mineral sample of FIG. 1.
Figure 4B:
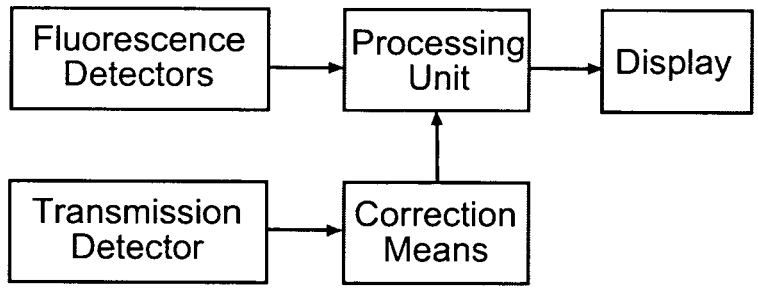

Referring to FIG. 1 to 4, a preferred embodiment of an apparatus 1 for X-ray fluorescence analysis of a mineral sample will be described. The apparatus comprises an outer casing 10 which houses an X-ray source 2, and two fluorescence detectors 4,5. Through an opening 8, preferably closeable by means of a lid, a door or the like, a sample container 3 can be inserted into the apparatus 1 in order to analyze a mineral sample contained in the sample container 3. The apparatus is preferably connected to an external display 7 in order to display the results of the X-ray fluorescence analysis to a user, a printer for printing the results, and/or other suitable user interfaces. Further, the display 7 may alternatively be integrated in the apparatus 1.

The X-ray source 2 may be a conventional X-ray tube equipped e.g. with a Söller collimator, comprising a stack of metal plates spaced a few tenths of a millimeter apart, to form a collimated beam. The X-ray source 2 generates an X-ray beam having a principal direction parallel to the plane in which the X-ray source 2 and the fluorescence detectors 4,5 are arranged.

The sample container 3 preferably has the form of a cone frustum and is arranged in front of the X-ray source 2, preferably at a small distance to avoid intensity loss of the X-ray beam. The longitudinal axis of the sample container 3 is preferably perpendicular to the plane in which the X-ray source and the fluorescence detectors 4,5 are arranged. Furthermore, the sample container 3 is preferably rotatable about its longitudinal axis. It can also preferably be translated along its longitudinal axis, thereby enabling the X-ray beam to irradiate portions of the sample container 3 having different diameters.

Further, the X-ray source 2 is preferably provided with controller means to automatically set the X-ray tube voltage based on the longitudinal position of the sample container 3. Thus, the energy of the X-ray beam may vary with the length of the irradiation path through the mineral sample.

The sample container 3 here has a height about 250 mm, and a diameter varying from 30 mm at the bottom to 80 mm at the top. Moreover, the sample container 3 is made of a material, such as plastic or glass, which is transparent to the X-rays and fluorescent radiation used.

As depicted in FIG. 1, the two fluorescence detectors 4,5 are preferably arranged on opposite sides of the sample container 3. Both fluorescence detector 4,5 face the sample container and are arranged at an essentially right angle to the principal direction of the X-ray beam. The fluorescence detectors 4,5 can be conventional solid-state detectors preferably with a high degree of energy dispersion. Each fluorescence detector 4,5 is connected to the processing unit. The processing unit may be a conventional CPU, on which runs software in order process input data to obtain the resulting X-ray fluorescence analysis. A multichannel analyzer (MCA) can also be provided between the fluorescence detectors 4,5 and the processing unit.

When a mineral sample is to be analyzed it is filled into the sample container 3, which is then sealed and inserted into the apparatus 1. Beginning the analysis, the sample container 3 may e.g. be located in its lower longitudinal end position, and the X-ray tube voltage is set to 160 kVp. Thus, the X-ray source 2 generates an X-ray beam, which irradiates the upper portion of the sample container 3 having a diameter of 80 mm. The sample container 3 is then gradually translated along its longitudinal direction so that various portions of the sample container 3 are irradiated, thus changing the length of the irradiation path through the mineral sample. During translation, the X-ray tube voltage is changed accordingly in order to adapt the energy of the X-ray beam to the excitation energy for the element currently analyzed. At the end of the analysis, the X-ray beam is directed at the lower portion of the sample container 3 having a diameter of 30 mm and the X-ray tube voltage is now 40 kVp. The translation can be continuous, but it could equally well be performed by positioning the sample container 3 in a series of positions along the longitudinal axis, such as two, three or more positions, and for each position irradiate the sample container 3. For example, two positions could be utilized by first irradiating the sample container 3 in its lower longitudinal end position, then shifting the sample container 3 to its upper longitudinal end position where it is also irradiated.

Throughout the irradiation, the sample container 3 is preferably rotated around its longitudinal axis in order to improve the accuracy of the X-ray fluorescence analysis. The rotational speed is typically 5 to 20 rpm.

As the mineral sample is irradiated, fluorescent radiation is emitted by the elements contained therein. The fluorescent radiation is measured by the fluorescent detectors 4, 5, each producing a signal containing a continuous distribution of pulses, the voltages of which are proportional to the incoming photon energies. This signal can be processed by the multi-channel analyzer and/or the processing unit to obtain a spectrum representing the elements contained in the mineral sample. If the apparatus 1 has been properly calibrated against known levels of the respective element the amount of each element can be quantified. The result can be displayed to the user on the display 7.

As illustrated in FIG. 1, the apparatus 1 may further comprise a transmission detector 9, wherein the X-ray source 2 and the transmission detector 9 are arranged on opposite sides of the sample container 3. The transmission detector 9 may preferably be located along the principal direction of the X-ray beam in such a way that it faces the X-ray source 2, to best measure transmission of X-rays through the irradiation path of the sample container. Furthermore, the transmission detector 9 can be a conventional solid-state detector preferably with high sensitivity. During analysis the transmission detector 9 measures the X-rays passing through the mineral sample, and e.g. produces a signal containing a continuous distribution of pulses, the voltages of which are proportional to the incoming X-rays. The output signal of the transmission detector is fed to correction means, where the X-ray fluorescence analysis can be adjusted for variations in compositions of the mineral sample as will be explained below.

The pulse number measured by the transmission detector 9 relates to the attenuation of the X-ray beam as described by equation 1:

$$N = N_0 \cdot \exp(-\mu \cdot d) \tag{Eq. 1}$$

where

N is the pulse number measured by the transmission detector;

$N_0$ is the pulse number that would be detected with no attenuation present;

$\mu$ is the linear attenuation coefficient cm$^{-1}$; and d is the diameter of the sample.

The diameter d of the sample container, and the pulse numbers N and $N_0$ are all known. Thus, the attenuation coefficient for the mineral sample can be computed using equation 2:

$$\mu = \frac{\ln\left(\frac{N_0}{N}\right)}{d} \tag{Eq. 2}$$

The measured pulse number for the fluorescent radiation is adjusted for variations in composition of the mineral sample according to equation 3:

$$N_{corr} = N_{0corr} \cdot \exp(\mu \cdot d) \tag{Eq. 3}$$

where $N_{corr}$ is the corrected pulse number; and $N_{0corr}$ is the pulse number measured by the fluorescence detectors.

The correction is related to the attenuation of the fluorescent radiation, and provides an improved accuracy when determining the amounts of the various elements/materials. The intensity of the primary radiation can be established by means of calibration tests, which may be repeated regularly, such as once a day, or each time the apparatus is restarted.

A more accurate compensation for fluorescent attenuation can be achieved by separating the various components of the fluorescent radiation utilizing an energy spectrum analyzer for separately measuring the $K_\alpha$ and $K_\beta$ components of the fluorescent X-rays. Even in this case, with a separation of the K radiation in alfa and beta components, a correction for different attenuation of the radiation can be made, as discussed above. To this end, an effectiv $\mu$ can be determined from the attenuation measurements, and can subsequently be corrected for the actual energy of the K radiation. The energies for $K_\alpha$ and $K_\beta$ components of the fluorescent X-rays are fixed, and previously known for various elements and materials.

The present invention has now been disclosed with reference to certain embodiments. However, as would be readily acknowledged by a person skilled in the art, other embodiments than the ones disclosed above are equally possible. For example, the number of fluorescence detectors may vary, and be fewer or more than two, and the number of transmission detectors may also vary. Also the fluorescence detectors do not have to be arranged in the same plane as the sample container. Still further, the sample may be rotated and translated in various fashions during the irradiation, and many different irradiation paths may be provided. In an alternative embodiment the X-ray source may also be translated and/or rotated while the sample container is held still, thereby providing the same relative motion as when the sample container is moved. Further, the sample container may take many different shapes and dimensions. Such and other modifications of the above-discussed embodiments must be considered to be encompassed by the invention as defined by the appended claims.

The invention claimed is:

1. An apparatus for X-ray fluorescence analysis of a mineral sample comprising:
    an X-ray source configured to generate an X-ray beam to irradiate the mineral sample;
    at least one fluorescence detector configured to measure fluorescent radiation emitted by the mineral sample when irradiated by the X-ray beam;
    a processing unit configured to provide an analysis of the mineral sample based on the measurements made by the at least one fluorescence detector;
    a sample container configured to hold the mineral sample during the irradiation, wherein the sample container is configured to provide at least two different irradiation paths through said mineral sample during irradiation; and
    a controller configured to adjust an X-ray tube voltage of said X-ray source in accordance with a length of the at least two different irradiation paths.

2. The apparatus according to claim 1, wherein said at least two different irradiation paths have different lengths through said mineral sample.

3. The apparatus according to claim 1, wherein said sample container has a uniform cross-section.

4. The apparatus according to claim 1, wherein said sample container has a non-uniform cross-section.

5. The apparatus according to claim 1, wherein the sample container is configured to rotate.

6. The apparatus according to claim 1, wherein the sample container has a tapered form.

7. The apparatus according to claim 1, wherein the sample container is arranged to provide at least five different irradiation paths through the mineral sample during irradiation.

8. The apparatus according to claim 1, wherein the length of the at least two different irradiation paths through said mineral sample is in a range of between 30 mm and 80 mm.

9. The apparatus according to claim 1, wherein said X-ray tube voltage is a value between 40 kVp and 160 kVp.

10. The apparatus according to claim 1, further comprising:
- a transmission detector configured to measure X-ray transmission through the mineral sample during irradiation; and
- a correction unit configured to correct the measured fluorescent radiation due to variations in composition of the mineral sample based on the measurements made by the transmission detector.

11. The apparatus according to claim 9, comprising an energy spectrum analyzer for separately measuring $K\alpha$ and $K\beta$ components of the fluorescent X-rays.

12. The apparatus according to claim 10, wherein the at least one X-ray fluorescence detector and the transmission detector are arranged separated from each other.

13. The apparatus according to claim 1, wherein a first and a second X-ray fluorescence detector are arranged on opposite sides of said sample container.

14. The apparatus according to claim 1, wherein said apparatus is portable.

15. A method for X-ray fluorescence analysis of a mineral sample comprising the steps:
- providing a mineral sample in a sample container;
- irradiating said mineral sample with an X-ray beam;
- measuring fluorescent radiation emitted by the mineral sample when irradiated by the X-ray beam;
- providing an analysis of the mineral sample based on the measurements of the fluorescent radiation, wherein the sample container is configured to provide at least two different irradiation paths through said mineral sample during irradiation; and
- adjusting an X-ray tube voltage of an X-ray source generating said X-ray beam in accordance with a length of the at least two different irradiation paths.

16. The method according to claim 15, wherein said at least two different irradiation paths have different lengths through said mineral sample.

17. The method according to claim 15, wherein the sample container is configured to rotate.

18. The method according to claim 15, wherein the sample container has a tapered form.

19. The method according to claim 1, wherein the sample container is arranged to provide at least five different irradiation paths through the mineral sample during irradiation.

20. The method according to claim 15, further comprising:
- measuring X-ray transmission through the mineral sample during irradiation; and
- correcting the measured fluorescent radiation due to variations in composition of the mineral sample based on the measurements made by the transmission detector.

21. The method according to claim 20, further comprising:
- separately measuring $K\alpha$ and $K\beta$ components of the fluorescent X-rays.

22. The method according to claim 15, wherein the fluorescence is measured on opposite sides of said sample container.

23. The apparatus according to claim 3, wherein the uniform cross section is a circular cross section.

24. The apparatus according to claim 5, wherein the sample container is configured to rotate during said irradiation.

25. The apparatus according to claim 7, wherein the at least two irradiation paths are of different lengths through said mineral sample.

26. The apparatus according to claim 13, wherein the first and second X-ray fluorescence detectors are arranged at essentially right angles to a principal direction of the X-ray beam.

27. The method according to claim 17, wherein the sample container is configured to rotate during said irradiation.

28. The method according to claim 19, wherein said at least five different irradiation paths are of different lengths through said mineral sample.

29. The method according to claim 22, wherein the fluorescence is measured at essentially right angles to a principal direction of the X-ray beam.

* * * * *